United States Patent [19]

Crawford

[11] 4,266,142
[45] May 5, 1981

[54] FLUID SYSTEM AND METHOD

[75] Inventor: Juan H. Crawford, Dublin, Ohio

[73] Assignee: AccuRay Corporation, Columbus, Ohio

[21] Appl. No.: 693,492

[22] Filed: Jun. 7, 1976

[51] Int. Cl.³ ............................................ G01N 21/88
[52] U.S. Cl. .................................... 250/572; 250/571
[58] Field of Search ............... 250/572, 571, 559, 308, 250/358 R

[56] References Cited

U.S. PATENT DOCUMENTS

| | | | |
|---|---|---|---|
| 1,978,589 | 10/1934 | McFarlane | 250/239 |
| 3,426,200 | 2/1969 | Lehman et al. | 250/308 |
| 3,489,008 | 1/1970 | Thorton et al. | 250/338 |
| 3,628,028 | 12/1971 | Thorsheim | 250/239 |
| 3,662,174 | 5/1972 | McMullen et al. | 250/358 |
| 3,742,216 | 6/1973 | Hahn | 250/308 |

OTHER PUBLICATIONS

Reba, "Applications of the Coanda Effect", *Scientific American*, vol. 214 #6, Jun. 1966, pp. 84–92.

*Primary Examiner*—David K. Moore
*Attorney, Agent, or Firm*—C. Henry Peterson

[57] ABSTRACT

A radiation device, such as an instrument for gauging a property of moving sheet materials, has a surface including window means in the path of radiation affecting the output of a radiation detector. The radiation transmission characteristics of the portion of the radiation path including the window means are maintained substantially constant so as to reduce the probability of error in the detector output response resulting from the presence of an unpredictable amount of extraneous radiation-absorbing or scattering material in the path or at the window means. A jet of fluid, such as compressed air, is formed in a manner such that the jet is attached to the surface by implementation of the Coanda effect and directed to flow over the window means. Typically the jet is initially directed away from the portion of the surface adjoining the window means. The jet is typically formed between an abruptly terminating wall and an attachment wall which gradually turns into the direction of the window location and effectively forms a continuation of the surface, whereby the jet is guided into a curved path to the location of the window means. This arrangement allows the jet-forming structure to be placed in a location, such as in a sunken area below the main portion of the surface, where it cannot interfere with the movement of the sheet material. Likewise it has been found not to interfere with the operation of a high-volume, constant temperature air blower which may be used concurrently to maintain constant atmospheric conditions in the radiation path adjacent to the window means.

38 Claims, 10 Drawing Figures

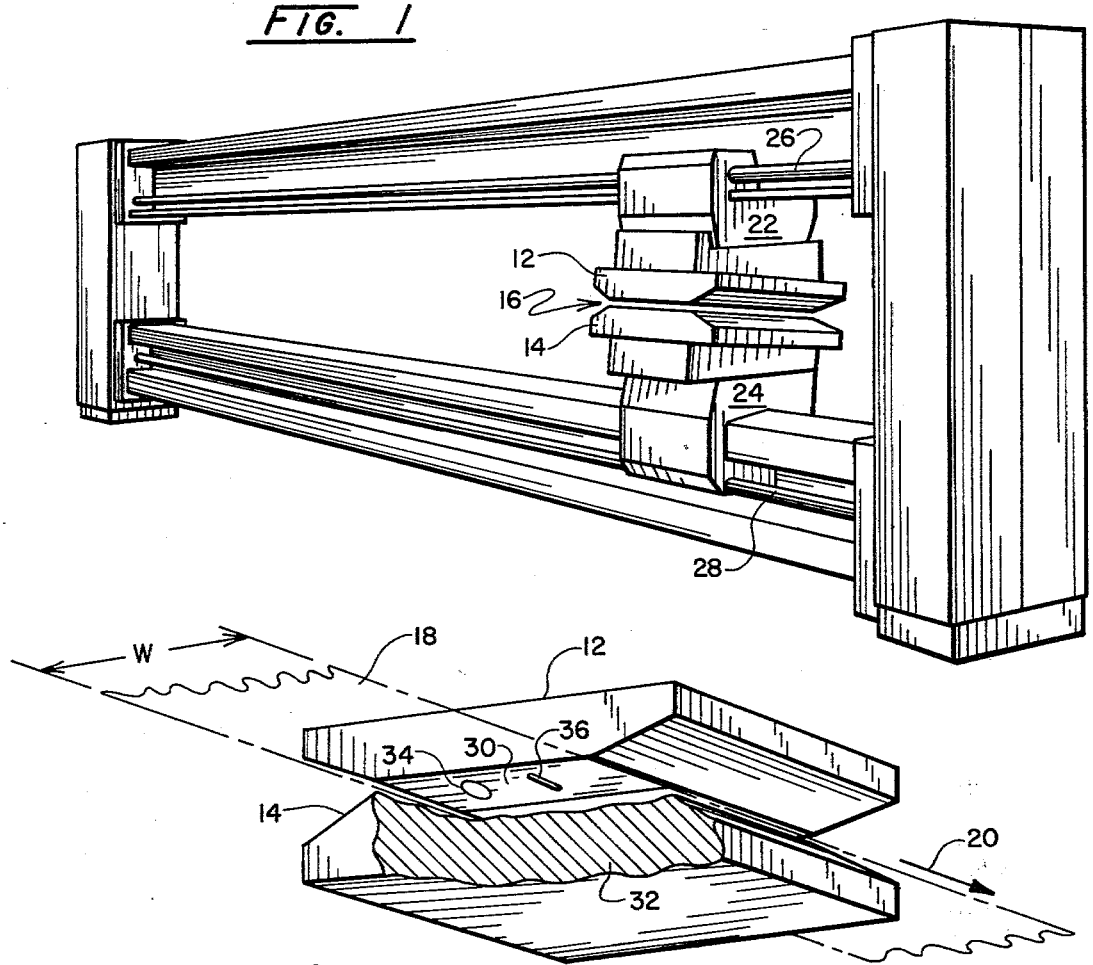
FIG. 1
FIG. 2
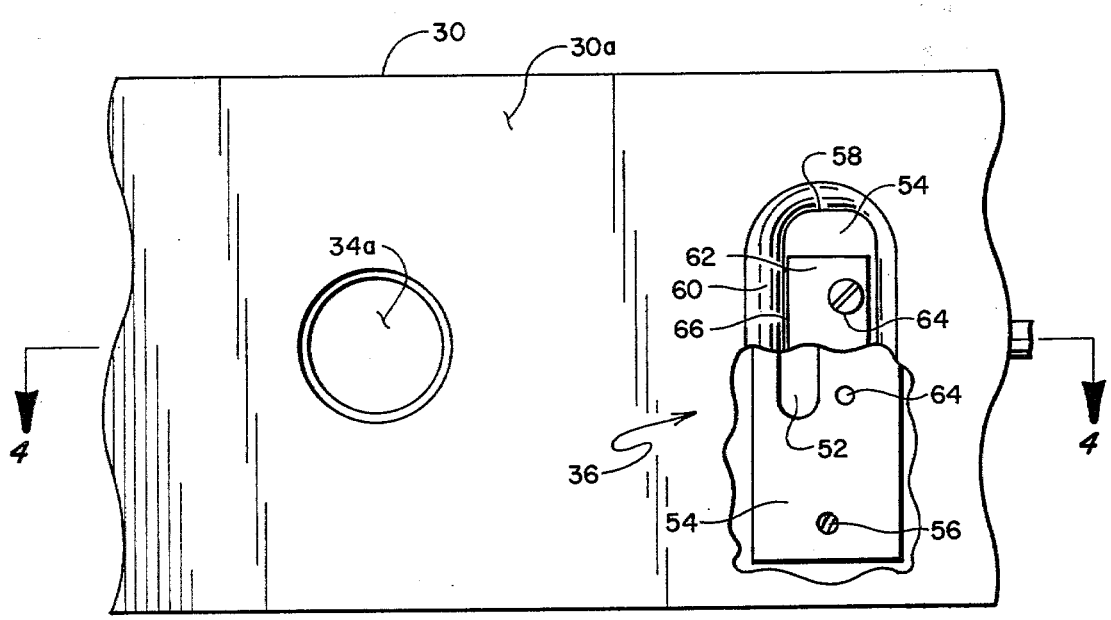
FIG. 3

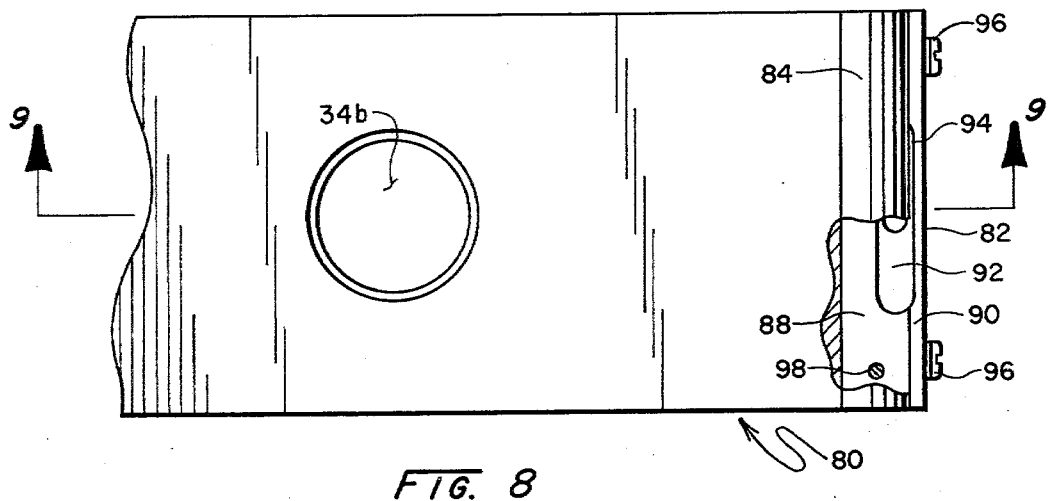
FIG. 8
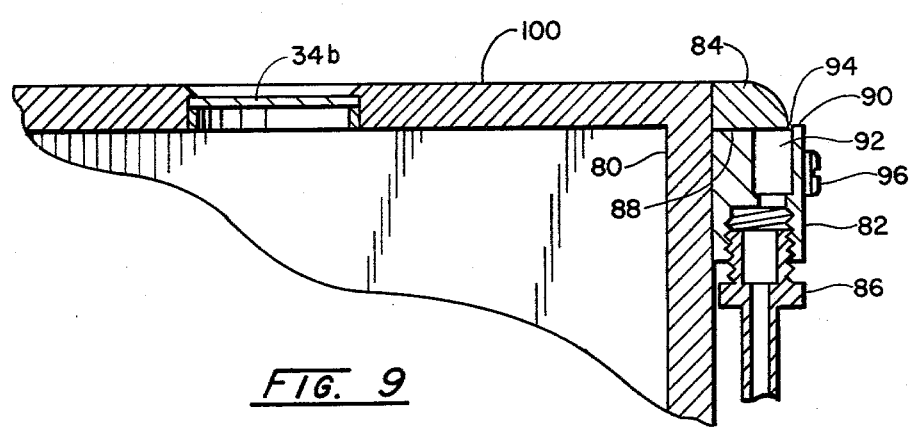
FIG. 9
FIG. 10

FLUID SYSTEM AND METHOD

This invention relates to a method and apparatus for excluding and removing extraneous matter from the path of radiation utilized by a radiation device. More particularly it relates to a method and apparatus utilizing the Coanda effect to direct a flow of fluid over a window means which transmits radiation affecting the output of a radiation detector. While the method and apparatus of the invention have many applications, they are particularly useful in connection with radiation gauges for measuring the properties of traveling sheet materials.

It is generally known, in the use of smoke detectors, for example, to produce a flow of a fluid such as clean air through the space adjacent to a radiation source and/or detector window in order to prevent or minimize the accumulation of extraneous matter on the window or windows, e.g., as shown by U.S. Pat. No. 3,628,028. A typical photoelectric arrangement for detecting sheet material is described in U.S. Pat. No. 1,978,589. An "air wipe" system adapted to perform the particularly difficult task of actually removing oil and other foreign matter from the source and detector windows of a sheet gauge, using air jets, is disclosed in U.S. Pat. No. 3,662,174. The somewhat different, but related "air gap conditioning" problem of preventing errors arising from changes in the mass of the air column between the source and the detector due to atmospheric pressure changes and the like has also been solved to a practical extent, as described in U.S. Pat. Nos. 3,426,200 and 3,742,216.

Air gap conditioning generally requires a fairly high volume of heated, relatively low pressure air which is rather ineffective to prevent or remove accumulation of extraneous matter on the windows. Effective air wiping has generally required a nozzle arrangement for aiming a flow of high-speed air at the window or the adjoining region. This has meant that the nozzle structure needed to protrude into the air gap region through which the traveling sheet had to travel, thereby risking damage to the sheet or to the gauge.

According to the present invention, in the use of a radiation device having a surface including window means in the path of radiation affecting the output response of a radiation detector, there is provided a method of, and apparatus for, maintaining substantially constant the radiation transmission characteristics of the portion of the radiation path including the window means and thereby reducing the probability of error in the detector output response resulting from the presence of an unpredictable amount of extraneous radiation-absorbing or scattering material in the path or at the window means, comprising forming a jet of fluid in a manner such that the jet is attached to the surface by implementation of the Coanda effect and directed to flow over the window means.

Typically the jet is initially confined between an abruptly terminating wall and an attachment wall effectively forming a continuation of the surface. The jet may be initially formed at a location spaced from the location of the window means, and pointed away from the portion of the surface adjoining the window means. The attachment wall typically gradually turns into the direction of the window location and forms a continuation of the surface, whereby the jet is guided into a curved path to the location of the window means.

The radiation device is typically an instrument adapted to respond to a property of a sheet material traveling along a substantially planar course, and the jet is initially formed at a location spaced at a greater distance from the course than the portion of the surface adjoining the window means, so that the jet can be formed without interfering with the sheet material even if the course thereof happens to coincide with the adjoining surface portion due to sheet flutter, movement of the instrument or the like. The jet may be initially pointed in the direction of the course of the sheet material.

The fluid is typically a compressed gaseous fluid such as filtered air under a pressure between about 5 and 60 psig.

The initial jet-forming walls typically converge in the direction of fluid flow.

The jet may be formed as a substantially planar sheet of fluid having an extended width and a thickness between about 0.001 and 0.030 inches.

The jet may be formed in a sunken area below the main portion of the surface, with one wall of the sunken area constituting a recessed minor portion of the surface, and with the jet being formed between the abruptly terminating wall and said one wall.

Where the detector output response is subject to error as a result of unpredictable changes in the ambient atmospheric conditions of the portion of the radiation path adjacent to the window means, the method may comprise blowing a volume of substantially constant-temperature air into the radiation path and over the window, superimposed on the fluid from the jet which is attached to the surface. The jet of fluid will ordinarily provide a flow of air having a substantially smaller volume than the volume of constant-temperature air. The temperature of the constant-temperature air may be regulated and the temperature of the jet flow of air may be unregulated. The constant-temperature air may be heated and the jet flow of air may be substantially unheated.

Some of the objects of the present invention are to provide improved methods and apparatus for substantially excluding and removing extraneous matter from the path of radiation passing through a radiation window means and affecting the output of a radiation detector, to provide such methods and apparatus which are effective without the use of nozzles or parts that protrude into a region beyond the window or adjoining surface, using apparatus which is simple and inexpensive to manufacture and which can be easily attached to existing radiation devices, and to provide an effective air wipe method and apparatus which does not interfere with the operation of an apparatus for conditioning an extensive body of air in the radiation path.

Other objects and advantages will become apparent in the following detailed description of some exemplary embodiments of the invention, taken in conjunction with the appended drawings, in which:

FIG. 1 is a perspective view of a "scanning platform" which serves as a traversing support for sensors such as radiation gauges for measuring the properties of a traveling sheet of paper and the like.

FIG. 2 is a schematic, perspective representation of a portion of the scanning platform of FIG. 1, showing a typical location for a radiation gauge incorporating an air wipe system according to the present invention.

FIG. 3 is an orthographic view of the plate 30 of FIG. 2, showing the radiation transmissive window and surrounding surface together with the outlet side of the Coanda nozzle arrangement.

FIG. 8 is an orthographic view of a different arrangement of the air wipe system which is adapted for installation on the edge of a plate containing a radiation transmissive window, or on the side of a box-like housing for a radiation source or a detector.

FIG. 9 is a section on the line 9—9 of FIG. 8.

FIG. 10 is a schematic view, partly in section, showing the combination of a Coanda air wipe with an air gap conditioning blower.

Figure 4:
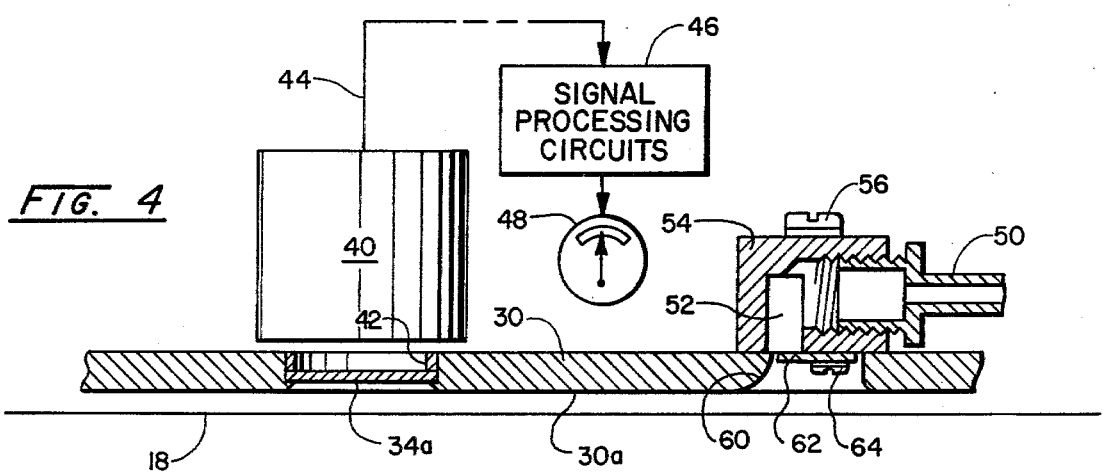
FIG. 4 is a section on the line 4—4 of FIG. 3, with a superimposed schematic representation of signal processing circuits and a readout device connected to a radiation detector.

Referring now to FIGS. 1 and 2, a modern "scanning platform" includes an upper sensor housing 12 and a lower sensor housing 14. The housings 12 and 14 are commonly separated by a one-half inch air gap 16, through which a sheet 18 travels while undergoing measurement by sensors installed in housings 12 and 14 of the scanning platform. Typically the sheet 18 is a sheet of paper being produced by a paper-making machine. The sheet 18 may have a width W up to 400 inches or more, and will be traveling in the direction of the arrow 20 in a planar course between housings 12 and 14 at a linear speed of perhaps 1800 feet per minute. Housings 12 and 14 have respective carriages 22 and 24, supported on tubular guides as at 26 and 28 which permit traversing the housings 12 and 14 across the width W of the sheet 18. While in FIG. 2 the sheet 18 is shown to have only a very narrow width W, the actual width is many times wider than housings 12 and 14, as is apparent from the length of the traversing guide tubes 26 and 28 which extend across the width of the sheet.

In the bottom portion of housing 12, next to the pass gap 16 for sheet 18, there is shown a rectangular plate 30 which supports and contains a sensor module. As shown, housing 12 includes space for mounting three such plates and associated sensor modules. For simplicity, the lower housing 14 is shown with a cut-away portion 32 in order to make the plate 30 visible. For simplicity, the cut-away portion 32 is lined as though the housing portion 14 were solid, but in fact the housing 14 is hollow and contains mounting space for three modules and their associated mounting plates as at 30 which match the plates and modules in the upper housing 12.

Perhaps the most commonly used module is a radiation device or devices. Such devices generally include one or more window means such as window means 34 in FIG. 2 whereby radiation is either directed at the sheet 18 or received from the sheet. In a backscatter configuration, radiation will be directed from the interior of housing 12 to impinge on the sheet 18, and back-scattered radiation returned through window 34 will be detected to provide a measurement of some property of the sheet 18. In a transmission gauge, a radiation source (not shown) may be mounted in the lower housing 14 in order to direct a beam of radiation upwardly through a window means facing window means 34 in the upper housing 12. The radiation thus transmitted through the sheet 18 will enter through window 34 and be detected in order to provide a measurement of the sheet property, for example, the basis weight of paper.

Another example of a radiation device to which the present invention may appertain is described in a paper by B. Y. Cho and O. L. Utt entitled "A New $TiO_2$ Compensated X-Ray Ash Sensor for Paper", presented at the Industry Oriented Conference and Exhibit in Milwaukee, Wis., Oct. 6-9, 1975, ISA Paper No. 75-611. A further example of a radiation device is an infrared radiation gauge for thin plastic films, such as that described in the copending application of Paul Williams et al, Ser. No. 673,534, filed Apr. 5, 1976, now U.S. Pat. No. 4,027,161. The radiation device may be one of the type which detects radiation spontaneously emitted from the sheet 18 in order to measure its temperature, for example as described in U.S. Pat. No. 3,489,008.

Any of these devices may be subject to error if extraneous radiation-absorbing or scattering material is present in the radiation path or collected at the window means 34. Such material is commonly carried by the traveling sheet 18 or accompanies the boundary layer of air carried along with the sheet as a result of its movement. The foreign matter may collect on the outer surface of a window formed of radiation-permeable material, or it may simply float through the air gap or pass gap 16 in the vicinity of the window means, thereby constituting an attenuator or scatterer in the path of the radiation. Attenuation or scattering of radiation, either in the beam which is directed toward the sheet or in the beam which is received from the sheet may produce an error in the measurement provided by the instrument.

Such extraneous radiation-absorbing or scattering material can be excluded and/or removed from the radiation path by the novel method and apparatus of this invention through the use of a jet of fluid ejected from a Coanda nozzle arrangement 36 as hereinafter described. For an historical and background description of the Coanda effect and some of its applications, reference can be made to an article by Reba, Imants, "Applications of the Coanda Effect", *Scientific American*, Volume 214, No. 6, June 1966, pages 84–92. In addition to the uses of the Coanda effect in propulsion applications, it is employed in fluidic amplifiers and oscillators and in air-flow amplifiers such as the Transvector air-flow amplifiers which are marketed by Vortec Corporation of Cincinnati, Ohio. The use of the Coanda effect in combination with a sound recording and reproducing transducer is described in U.S. Pat. No. 2,921,144.

A specific embodiment of a method and apparatus according to this invention is illustrated in detail in FIGS. 3 to 6. Herein it is seen that the plate 30 of FIG. 2 has a surface 30a including window means in the path of radiation affecting the output response of a radiation detector 40. The window means as here illustrated is a disc 34a of window material which is slightly recessed below the main surface 30a, as appears more particularly in FIG. 4, and held in place by a retainer ring 42.

Radiation entering through the radiation-penetrable window 34a impinges on detector 40, which produces an output response in the form of a signal fed over line 44 to signal processing circuits 46 and thence, if desired, to an appropriate meter 48 or other suitable readout device. The presence of an extraneous radiation-absorbing or scattering material accumulated on window 34a or elsewhere in the radiation path can result in an error in the detector output response on line 44. While small amounts of such extraneous material uniformly distributed on window 34a can be compensated electrically by the well-known process of standardization carried out electrically in signal processing circuits 46 to eliminate the bulk of the error, this cannot be done effectively where the amount and distribution of the extraneous material is unpredictable.

In order to maintain substantially constant the radiation transmission characteristics of the portion of the radiation path including the window means 34 and thereby reduce the probability of error in the detector output response, a jet of fluid is formed in a manner such that the jet is attached to surface 30a including the surface of window 34a and directed to flow over the window.

To this end, a fluid which is typically compressed air is fed through an inlet pipe fitting 50 into a plenum chamber 52. Chamber 52 may be simply a milled opening in an aluminum block 54 which is secured to the top side of plate 30 by screws as at 56. Block 54 bridges a rectangular opening 58 with rounded corners which is milled into plate 30. The side of the milled opening 58 is gradually sloped on the side next to the window 34a to form an attachment wall 60 for the Coanda jet. The opposite side and the ends of opening 58 are rounded on the edges next to the main portion of surface 30a, but do not have the same gradual cut-back or gently rounded shape as the attachment wall 60 next to the window.

The bottom opening into plenum chamber 52 is substantially covered by a cover plate 62 which is secured to block 54 by screws 64.

A jet of fluid from pipe 50 and plenum chamber 52 is ejected through a slit 66 between the cover plate 62 and the attachment wall 60. The edge of the cover plate 62 forms an abruptly terminating wall 68. The jet as initially formed between attachment wall 60 and the abruptly terminating wall 68 is initially pointed away from the portion of the surface 30a adjoining the window means, that is, in the direction of the arrow 70, aimed in the direction of the course of the sheet material 18. However, due to the Coanda effect the jet attaches itself to the attachment wall 60 which gradually turns in the direction of the window location indicated by the arrow 72. The jet is thereby guided into a curved path to the location of the window means. The jet is initially formed in a sunken area which constitutes a recessed minor portion of the surface 30a, and is thus formed at a greater distance from the course of sheet material than the portion of the surface 30a adjoining the window means. Hence, the jet is formed without the use of nozzles or the like which could interfere with the sheet material 18 even though due to flutter of the sheet it could ride directly against the adjoining surface portion 30a.

Figure 6:
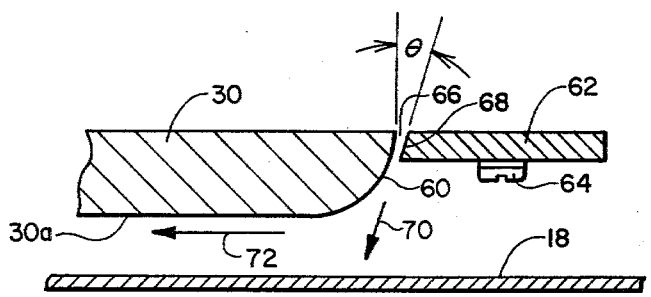
FIG. 6 is a schematic enlargement of a portion of FIG. 4, showing a typical arrangement of the abruptly terminating wall and the attachment wall whereby the initial jet is formed.
Figure 7:
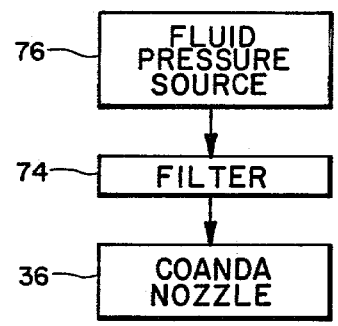
FIG. 7 is a block diagram of a fluid pressure source, a filter and a Coanda nozzle, illustrating the routing of fluid under pressure from the source through the filter to the nozzle.

As is particularly shown in FIG. 6, the cover plate 62 is beveled at an angle θ which matches the radius of the attachment wall 60 in such a way that the walls converge in the direction of fluid flow. The slit 66 has an extended width but the spacing between walls 60 and 68 is desirably between about 0.001 and 0.030 inches. Hence the jet as initially formed is a sheet of fluid having an extended width and a small thickness. If the jet is too thin, it may not provide sufficient fluid flow to effect the wiping action, but on the other hand if the thickness is too great it will result in excessive fluid consumption. The best compromise or optimum value has been found to be about 0.003 to 0.004 inches in the configurations tested. If the jet-forming slit is too narrow it not only may supply insufficient air but it may be subject to plugging by small particles of foreign material in the fluid supplied by the fluid pressure source. To mitigate this problem, a suitable filter 74 is installed between the fluid pressure source 76 and the nozzle, as shown in FIG. 7.

Typically, the fluid source 76 provides a supply of compressed air under a pressure between about five and sixty psig. For most of the applications tested, a pressure in the vicinity of about five psig has provided satisfactory results.

Figure 5:
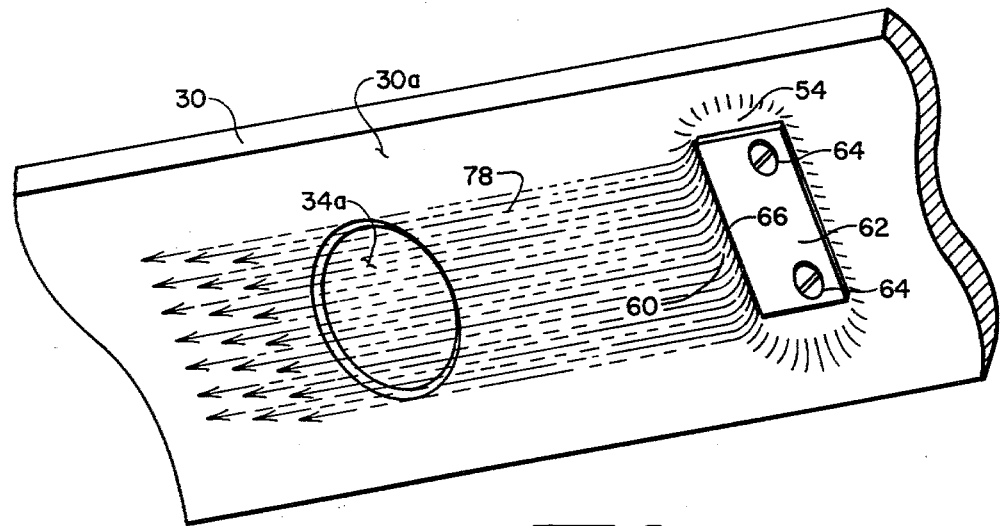
FIG. 5 is a schematic drawing, in a perspective view similar to a portion of FIG. 2, showing a representation of a sheet of air issuing from the Coanda nozzle and flowing over the surface of the plate and the window.

As shown in FIG. 5, the sheet of air 78 is persistently attached to the surface 30a including the slightly recessed continuation of this surface formed by the outside of window 34a.

As shown by FIGS. 8 and 9, an alternate arrangement of a Coanda nozzle has been designed particularly for attachment to the edge of a plate or to the edge of a box-like housing 80 for a radiation source of a radiation detector. The Coanda jet nozzle assembly basically comprises an aluminum body block member 82, an air flow cover 84 and an air line connection 86. A stepped-down portion 88 is milled out of the top of block 82 to accommodate the air flow cover 84, leaving an upwardly extending flange 90 to protrude above the bottom surface (indicated at 88 in FIG. 9) of the cover 84. A milled slot 92 in the body block 82 forms a plenum communicating with the air line connection 86. The slot 92 removes a portion of the width of flange 90, so that while the cover 84 abuts the flange 90 at both ends, a slit 94 is formed where the cover 84 bridges the slot 92. A slit width between about 0.003 and 0.007 inches has been found satisfactory for most applications.

The block 82 is secured to the housing 80 with screws 96. The cover 84 is secured to block 82 by screws as at 98 (shown in section) which extend vertically through block 82 and are threaded into tapped holes (not shown) in the cover 84.

In the arrangement of FIGS. 8 and 9, the Coanda jet is formed between the abruptly terminating wall provided by flange 90 and an attachment wall provided by the rounded surface of cover 84. The cover provides a surface which gradually turns in the direction of the window 34b.

The assembly shown in FIGS. 8 and 9 including the body 82 and cover 84 somewhat resembles the Curtain Transvector air flow amplifier marketed by Vortec Corporation mentioned above. The Curtain Transvector device is designed to entrain a high volume of the surrounding air in order to provide a maximum air flow for drying or cooling moving webs of material such as paper or plastic films. The device of FIGS. 8 and 9, however, is designed to form a very thin sheet of air which adheres closely to the surface 100 including the surface of window 34b in order to produce an efficient wiping action.

FIG. 10 illustrates an arrangement which is provided according to the invention for a radiation device wherein the detector output response is subject to error as a result of unpredictable changes in the ambient atmospheric conditions of the portion of the radiation path adjacent to a window means, for example window 34c. Compressed air from a pressure source 76 (FIG. 7)

through filter 74 is supplied via pipe 102 to a plenum chamber 104. The Coanda jet is formed between a plenum cover plate 106, providing the abruptly terminating wall, and the curved attachment wall 108 which directs the jet over the window 34c via the adjoining surface 110. This structure is similar to, and may be the same as, that used in FIGS. 3 through 6. The Coanda jet constitutes a thin sheet of air which adheres closely to the surface 110 and the top surface of the window 34c. The air gap conditioning system comprises a rather conventional arrangement 112 of a blower and heater similar to an oversized hair dryer. The air provided by unit 112 through nozzle 112a is conventionally thermostatically controlled to a temperature higher than the environmental temperature. This air is blown into the radiation path and over the window, superimposed on the layer of air from the Coanda jet which is attached to the surface. Because of the small volume and the close attachment to the surface of the sheet of air from the Coanda nozzle, it does not interfere substantially with the operation or the effectiveness of the air gap conditioning system.

While the invention has been described and illustrated in only a few specific embodiments, such illustration and description is meant to be illustrative only and not restrictive since obviously many changes, modifications and additional embodiments can be made without departing from the spirit and scope of the invention. For example, while the attachment wall for the Coanda jet has been illustrated only in the form of a smoothly rounded curved surface, the attachment wall can be faceted or made up of a number of adjoining planar surfaces.

What is claimed is:

1. In the use of a radiation device having a surface including window means in the path of radiation affecting the output response of a radiation detector, the method of maintaining substantially constant the radiation transmission characteristics of the portion of the radiation path including the window means and thereby reducing the probability of error in the detector output response resulting from the presence of an unpredictable amount of extraneous radiation-absorbing or scattering material in the path or at the window means, comprising
forming a jet of fluid in a manner such that the jet is attached to the surface by implementation of the Coanda effect and thereby directed to flow over the window means.

2. A method as in claim 1 which comprises initially confining the jet between an abruptly terminating wall and an attachment wall effectively forming a continuation of the surface.

3. A method as in claim 1 wherein the jet is initially formed at a location spaced from the location of the window means, comprising pointing the initially-formed jet away from the portion of the surface adjoining the window means.

4. A method as in claim 3 wherein the jet is initially formed between an abruptly terminating wall and an attachment wall which gradually turns into the direction of the window location and which forms a continuation of the surface, whereby the jet is guided into a curved path to the location of the window means.

5. A method as in claim 4 wherein the radiation device is an instrument adapted to respond to a property of a sheet material traveling along a substantially planar course, comprising initially forming the jet at a location spaced at a greater distance from the course than the portion of the surface adjoining the window means, so that the jet can be formed without interfering with the sheet material even if the course thereof happens to coincide with the adjoining surface portion.

6. A method as in claim 5 wherein the jet is initially pointed in the direction of the course of the sheet material.

7. A method as in claim 5 wherein the fluid is a compressed gaseous fluid.

8. A method as in claim 7 wherein the fluid is under a pressure between about 5 and 60 psig.

9. A method as in claim 7 wherein the fluid is compressed air.

10. A method as in claim 8 wherein the compressed air is filtered.

11. A method as in claim 4 wherein the initial jet forming walls converge in the direction of fluid flow.

12. A method as in claim 1 wherein the jet is formed as a substantially planar sheet of fluid which is initially confined between an abruptly terminating wall and an attachment wall effectively forming a continuation of the surface.

13. A method as in claim 1 wherein the jet is formed as a sheet of fluid having an extended width and a thickness between about 0.001 and 0.030 inches.

14. A method as in claim 1 wherein the jet is formed in a sunken area below the main portion of the surface.

15. A method as in claim 14 wherein one wall of the sunken area constitutes a recessed minor portion of the surface, comprising forming the jet between an abruptly terminating wall and said one wall.

16. A method as in claim 1 wherein the detector output response is subject to error as a result of unpredictable changes in the ambient atmospheric conditions of the portion of the radiation path adjacent to the window means, comprising,
blowing a volume of substantially constant-temperature air into the radiation path and over the window, superimposed on the fluid from the jet which is attached to the surface.

17. A method as in claim 16 wherein the jet of fluid is a flow of air having a substantially smaller volume than the volume of constant-temperature air.

18. A method as in claim 17 wherein the temperature of the constant-temperature air is regulated and the temperature of the jet flow of air is unregulated.

19. A method as in claim 17 wherein the constant-temperature air is heated and wherein the jet flow of air is substantially unheated.

20. In a radiation device having a surface including window means in the path of radiation affecting the output response of a radiation detector, the improvement for maintaining substantially constant the radiation transmission characteristics of the portion of the radiation path including the window means and for thereby reducing the probability of error in the detector output response resulting from the presence of an unpredictable amount of extraneous radiation-absorbing or scattering material in the path or at the window means, comprising
means for forming a jet of fluid in a manner such that the jet is attached to the surface by implementation of the Coanda effect and thereby directed to flow over the window means.

21. Apparatus as in claim 20 wherein the jet forming means comprises
an abruptly terminating wall, an attachment wall effectively forming a continuation of the surface, and means for ejecting a stream of the fluid between the walls.

22. Apparatus as in claim 20 wherein the jet forming means is spaced from the location of the window means, and wherein the jet forming means initially aims the jet away from the portion of the surface adjoining the window means.

23. Apparatus as in claim 22 wherein the jet forming means comprises an abruptly terminating wall, and an attachment wall which is gradually turned into the direction of the window location and which forms a continuation of the surface whereby the jet is guided into a curved path to the location of the window means.

24. Apparatus as in claim 23 wherein the radiation device comprises an instrument adapted to respond to a property of a sheet material traveling along a substantially planar course, and wherein the jet forming means is located at a greater distance from the course than the portion of the surface adjoining the window means, whereby the jet forming means does not interfere with the sheet material even if the course thereof happens to coincide with the adjoining surface portion.

25. Apparatus as in claim 24 wherein the jet forming means initially aims the jet in the direction of the course of the sheet material.

26. Apparatus as in claim 24 wherein the fluid is a compressed gaseous fluid.

27. Apparatus as in claim 24 comprising means for supplying the fluid to the jet-forming means under a pressure between about five and sixty psig.

28. Apparatus as in claim 27 wherein the fluid supply means comprises a source of compressed air.

29. Apparatus as in claim 28 comprising means for filtering the compressed air supplied to the jet-forming means.

30. Apparatus as in claim 21 wherein the initial jet forming walls converge in the direction of fluid flow.

31. Apparatus as in claim 20 for forming the jet as a substantially planar sheet of fluid, comprising an abruptly terminating wall, an attachment wall effectively forming a continuation of the surface, and means for initially confining the fluid between said walls while forming the jet.

32. Apparatus as in claim 20 wherein the jet-forming means forms the jet as a sheet of fluid having an extended width and a thickness between about 0.001 and 0.030 inches.

33. Apparatus as in claim 20 comprising means for mounting the jet-forming means in a sunken area below the main portion of the surface.

34. Apparatus as in claim 33 wherein one wall of the sunken area constitutes a recessed minor portion of the surface, comprising an abruptly terminating wall forming with said one wall a jet-defining orifice.

35. Apparatus as in claim 20 wherein the detector output response is subject to error as a result of unpredictable changes in the ambient atmospheric conditions of the portion of the radiation path adjacent to the window means, comprising means for blowing a volume of substantially constant-temperature air into the radiation path and over the window, superimposed on the fluid from the jet which is attached to the surface.

36. Apparatus as in claim 35 comprising means for forming the jet of fluid as a flow of air having a substantially smaller volume than the volume of constant-temperature air.

37. Apparatus as in claim 36 comprising means for regulating the temperature of the constant-temperature air.

38. Apparatus as in claim 37 comprising means for heating the constant-temperature air.

* * * * *